United States Patent [19]

Rosenthaler et al.

[11] Patent Number: 5,169,773
[45] Date of Patent: Dec. 8, 1992

[54] MONOCLONAL ANTIBODIES TO CYCLOSPORINS

[75] Inventors: Joachim Rosenthaler, Oberwil; Roland Wenger, Riehen; Philipp E. Ball, Binningen; Max H. Schreier; Valérie Quesniaux, both of Basel, all of Switzerland

[73] Assignee: Sandoz Ltd., Basel, Switzerland

[21] Appl. No.: 265,374

[22] Filed: Oct. 31, 1988

Related U.S. Application Data

[63] Continuation of Ser. No. 784,913, Oct. 4, 1985, abandoned.

[30] Foreign Application Priority Data

Oct. 4, 1984 [GB] United Kingdom ............ 842504
Jun. 20, 1985 [GB] United Kingdom ............ 8515673

[51] Int. Cl.$^5$ .............. C12N 5/20; C07K 15/28; G01N 33/53
[52] U.S. Cl. .............. 435/240.27; 530/388.9; 935/109; 935/110; 435/70.21; 435/172.2; 435/7.1
[58] Field of Search .............. 530/387, 388.9; 435/240.27, 7; 935/109–110

[56] References Cited

PUBLICATIONS

Quesniaux et al., Clinical Chemistry 33(1): 32–37, 1987.
Kipps et al. in Weir et al Eds., "Handbook of Immunology", vol. 4, Blackwell Sci. Publ. 1986.
Donatsch et al. J. Immunoassay 2(1): 19–32 1981.
Quesniaux et al. Immunol. Lett. 9: 99–104 1985.

Primary Examiner—John J. Doll
Assistant Examiner—Paula Hutzell
Attorney, Agent, or Firm—Gerald D. Sharkin; Robert S. Honor; Carl W. Battle

[57] ABSTRACT

Novel monoclonal antibodies capable of distinguishing between cyclosporins, e.g. Cyclosporine, and metabolites, e.g. Cyclosporins 17 and 18, are produced, e.g. starting from novel cyclosporins having an activated coupling group, e.g. activated carboxy group, e.g. (i) [(O-succinimidooxysuccinyl)-Thr]$^2$-Cyclosporine and (ii) [(N-ε-succinimidooxysuccinyl)-(D)Lys]$^8$-Cyclosporine. Cyclosporin starting materials required for the production of cyclosporins of type (ii), e.g. [(D)Lys]$^8$-Cyclosporine are also new and additionally have utility in the preparation of novel labelled cyclosporin derivatives, as well as antibodies and antisera generally. Also claimed are novel antigenic conjugates and hybridoma cell lines used in the production of antibodies and antisera as aforesaid as well as assay kits comprising novel antisera, antibodies and/or labelled cyclosporins as aforesaid.

6 Claims, No Drawings

MONOCLONAL ANTIBODIES TO CYCLOSPORINS

This is a continuation of application Ser. No. 06/784,913, filed Oct. 4, 1985 now abandoned.

The present invention relates to monoclonal antibodies to cyclosporins, in particular to monoclonal antibodies capable of distinguishing between cyclosporins and metabolites thereof and suitable for use in diagnostic/assay kits, as well as to novel hybridoma cell lines used in the production of said monoclonal antibodies and diagnostic/assay kits comprising said monoclonal antibodies. In addition the invention relates to novel cyclosporins and immunogenic conjugates comprising them, used for the generation of monoclonal antibodies as aforesaid and also useful for the generation of regular polyclonal antisera suitable for diagnostic/assay kit use, as well as to the product antisera and antibodies and diagnostic/assay kits comprising them. The invention also relates to labelled derivatives of said novel cyclosporins, themselves suitable for diagnostic/assay kit use, as well as to diagnostic/assay kits comprising them.

The cyclosporins comprise a class of structurally distinctive, cyclic, poly-N-methylated undecapeptides commonly possessing pharmacological, in particular immunosuppressive, anti-inflammatory and anti-parasitic activity. The first of the cyclosporins to be isolated was the naturally occurring fungal metabolite Cyclosporine, also known as cyclosporin A, of formula A

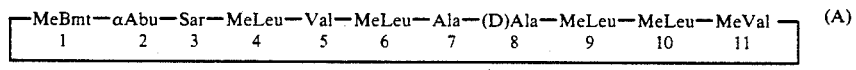

wherein -MeBmt- represents the N-methyl-(4R)-4-but-2E-en-1-yl-4-methyl-(L)threonyl residue of formula B

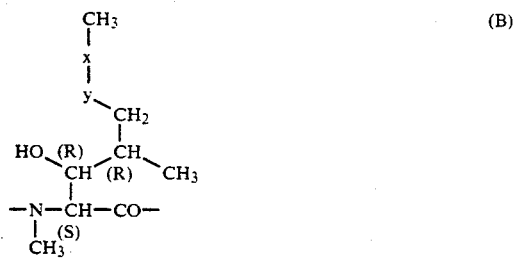

in which —x—y— is —CH=CH— (trans).

Since the original discovery of Cyclosporine, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes for example the naturally occurring cyclosporins A through Z [c.f. Kobel et al. European Journal of applied Microbiology and Biotechnology 14, 237-240 (1982) and poster presented by Traber et al., 24th. Interscience Conference on Antimicrobial Agents and Chemotherapy, Washington, Oct. 8-10, (1984)]; as well as various non-natural or artificial cyclosporins, including dihydro-cyclosporins (in which the group —x—y— of the -MeBmt- residue (see formula B above) is saturated, e.g. as disclosed in the U.S. Pat. Nos. 4,108,985; 4,210,581 and 4,220,641, cyclosporins in which the -MeBmt- residue is present in isomeric or N-desmethyl form [c.f. European patent no. 0 034 567 and "Cyclosporin A", Proc. Internat. Conference on Cyclosporin A, Cambridge (U.K.) Sep. 1981, Ed. D. J. G. White, Elsevier Press (1982)13 both describing the total-synthetic method for the production of cyclosporins developed by R. Wenger] and cyclosporins in which incorporation of variant amino acids at specific positions within the peptide sequence is effected. Examples of such cyclosporins as disclosed in the above art references include e.g. [Thr]$^2$-, [Val]$^2$-, [Nva]$^2$- and [Nva]$^2$-[Nva]$^5$-Cyclosporine (also known as cyclosporins C, D, G and M respectively) and dihydro-[Val]$^2$-Cyclosporine (also known as dihydrocyclosporin D).

[In accordance with now conventional nomenclature for the cyclosporins, these are defined throughout the present specification and claims by reference to the structure of Cyclosporine (i.e. cyclosporin A). This is done by first indicating those residues in the molecule which differ from those present in Cyclosporine and then applying the term "Cyclosporine" to characterise the remaining residues which are identical to those present in Cyclosporine. At the same time the prefix "dihydro" is employed to designate cyclosporins wherein the -MeBmt- residue is hydrogenated (-dihydro-MeBmt-), i.e. wherein —x—y— in formula B is —CH$_2$—CH$_2$—. Thus [Thr]$^2$-Cyclosporine is the cyclosporin having the sequence shown in formula A, but in which -αAbu- at the 2-position is replaced by -Thr-, and dihydro-[Val]$^2$-Cyclosporine is the cyclosporin having the sequence shown in formula A but in which -MeBmt- at position 1 is hydrogenated and -αAbu- at the 2 position is replaced by -Val-.

In addition, amino acid residues referred to by abbreviation, e.g. -Ala-, -MeVal- etc . . . are, in accordance with conventional practice, to be understood as having the (L)-configuration unless otherwise indicated. Residue abbreviations preceded by "Me", as in the case of -MeLeu- represent N-methylated residues. The individual residues of the cyclosporin molecule are numbered, as in the art, clockwise and starting with the residue -MeBmt- (or -dihydro-MeBmt-) in position 1. The same numerical sequence is employed throughout the present specification and claims.]

Because of their unique immunosuppressive activity, the cyclosporins have attracted very considerable attention not only in medical and academic circles, but also in the lay press. Cyclosporine itself is now commercially available and commonly employed to prevent rejection following allogenic organ, e.g. heart, heart-lung, kidney and bone-marrow transplant, as well as more recently in the treatment of various auto-immune and related diseases and conditions. Both dihydro-[Val]$^2$-Cyclosporin and [Nva]$^2$-Cyclosporin are under extensive clinical investigation as potential successors to Cyclosporine.

Dosaging of cyclosporins, e.g. Cyclosporine, however presents particular difficulties. Since metabolic conversion rates tend to be patient specific and the therapeutic range narrow, effective dosaging is highly subject specific and requires the establishment of appropriate individual serum levels. Regular monitoring of cyclosporin plasma concentrations is thus an essential prerequisit for effective treatment. To this end a number of high pressure liquid chromatography (HPLC), radioimmunoasssay (RIA) and fluoroimmunoassay (FIA) systems have been developed. However, HPLC methods, whilst highly specific are difficult and cumbersome to use in practice and the current commercially available RIA system based on sheep polyclonal antiserum has met with criticism because of its lack of specificity. Development of cyclosporin, e.g. Cyclosporine, specific monoclonal antibodies capable of distinguishing between therapeutically administered cyclosporins and their metabolites in man has accordingly for a long time been an urgent practical as well as purely scientific goal, since these would have the advantage of offering the same potential specificity as HPLC methodology, whilst retaining the advantage of ease of application provided by conventional immunoassay systems. In addition the provision of such cyclosporin-specific monoclonal antibodies would provide a vital new research tool permitting e.g. the comparative investigation of cyclosporin conformation and definition of cyclosporin receptor requirements etc . . . .

Since the original discovery of Cyclosporine, numerous attempts have been made to produce monoclonal antibodies reactive to cyclosporins. Since cyclosporins, e.g. Cyclosporine, themselves have little immunogenic activity, a common approach has been to proceed employing an immunogenic, e.g. hapten-protein, conjugate, e.g. derived by coupling of immunoglobulins via the hydroxy group available at -$Thr^2$- in [$Thr$]$^2$-Cyclosporine employing conventional coupling techniques, e.g. with EDCI [N-ethyl-N'-(3-dimethylaminopropyl)-carbodiimide.2HCl] or MCDI [N-cyclohexyl-N'-[$\beta$-(N-methylmorpholino)ethyl]-carbodiimide.p.toluene sulfonate] as coupling agent. Attempts in this manner have however failed and where monoclonal antibodies have been obtained, these have been found to have relatively low specificity for Cyclosporine, or to be specific with respect to the carrier protein or the coupling reagent employed rather than Cyclosporine, or to be highly cross-reactive with the coupling agent. In no instance has it proved possible to produce monoclonal antibodies identifiable as distinguishing between e.g. Cyclosporine and metabolites thereof, e.g. the metabolites Cyclosporine 17 and Cyclosporine 18 hereinafter specifically described In addition such attempts have led to the production of monoclonal antibodies to Cyclosporine of the type IgM only and hence in any event essentially inappropriate for use in any form of regular, e.g. clinical, assay kit. The production of monoclonal antibodies having specific reactivity with cyclosporins and capable of distinguishing between individual cyclosporins and their metabolites, e.g. between Cyclosporine and its metabolites in man, and suitable for use in an assay system has thus remained a major goal.

In accordance with the present invention it has now surprisingly been found that monoclonal antibodies reactive to cyclosporins and meeting the various objectives discussed above, in particular capable of distinguishing between cyclosporins and metabolites thereof, can be produced via essentially conventional immunisation/fusion/cloning techniques, employing immunogenic conjugates comprising a cyclosporin as hapten at the initial immunisation step, if the conjugate is prepared by coupling of the carrier to the cyclosporin by the agency of an activated coupling group, e.g. if conjugate synthesis is effected employing a cyclosporin having an activated coupling group as starting material. In particular using such immunogenic conjugates it is possible to obtain monoclonal antibodies capable of fine discrimination between cyclosporins and metabolites thereof bearing even single variant groupings on individual residues, e.g. in the case of Cyclosporine, being reactive with Cyclosporine while exhibiting low cross-reactivity with, for example, its metabolites Cyclosporine 17 and/or Cyclosporine 18.

In addition to at last providing the means for development of convenient monoclonal assay systems, e.g. for use in clinic, the present invention also provides a means for the further purification of cyclosporin metabolites and, since it may be anticipated that monoclonal antibodies will be obtainable by application of the general methods of the invention, which may mimic receptor sites, the characterisation of potential endogenous cyclosporin-like molecules. The significance of the present invention from both a practical and a purely scientific stand point will be thus readily apparent.

As indicated above, the immunogenic conjugates required in the practice of the invention are prepared by direct coupling of a carrier, e.g. protein molecule, with a cyclosporin by the agency of an activated coupling group. This may be effected, either by reaction of a carrier bearing an activated coupling group with a cyclosporin bearing an appropriate co-reactive substituent, e.g. hydroxy or amino group, e.g. as in the case of [$Thr$]$^2$-Cyclosporine or [(D)$Lys$]$^8$-Cyclosporine hereinafter described, or by reaction of a carrier with a cyclosporin having an activated coupling group, e.g. cyclosporin in which one of the amino acid residues present in the cyclosporin molecule has a side chain at the $\alpha$-carbon atom comprising or bearing an activated coupling group. The said conjugates thus comprise a cyclosporin, hapten moiety, directly linked to a carrier moiety, rather than via an intervening coupling agent residue, as in the case of immunogenic conjugates comprising a cyclosporin as hapten previously employed in the art, e.g. for raising regular polyclonal antisera.

By the term "activated coupling group" as used herein and throughout the accompanying claims is to be understood any group capable of direct reaction with an appropriate, co-reactive grouping, e.g. amino, hydroxy, thio group or the like, so as to provide a co-valent linkage, without requirement for use of a coupling agent to enable, effect or promote reaction. Thus in the case of cyclosporins bearing an "activated coupling group" this will be any group capable of direct reaction with a carrier molecule, e.g. protein molecule, to provide a co-valently linked conjugate with said carrier molecule, without requirement for use of a coupling reagent to enable, effect or promote coupling or reaction with said carrier molecule.

Groups suitable as activated coupling groups are well known in the art and include for example i) activated ester or activated carboxy groups, i.e. of formula —CO—OZ wherein Z is a carboxy activating group such as o- or p-nitrophenyl, 1-benztriazole, pentafluorophenyl or N-succinimido; ii) activated dithio groups, i.e. of formula —S—S—X wherein X is a dithio activating group such as 2-pyridyl; and iii) epoxy groups.

Suitable immunogenic conjugate carrier molecules, bearing an activated coupling group, e.g. epoxy group, as aforesaid, may be prepared in accordance with techniques known in the art, e.g. as described by Laumen et al., Tetrahedron Letters, 26 (4), 407–410(1985). In accordance with the general methods of the present invention it is however preferred that the activated coupling group be provided on the cyclosporin which is to be coupled with the carrier, rather than vice versa.

In principle the activated coupling group may be present at any position around the cyclosporin molecule. In so far as transformations at the 1-position are of particular significance in cyclosporin metabolism, or in so far as major cyclosporin metabolites, e.g. in the case of Cyclosporine, Cyclosporine 17 and Cyclosporine 18, exhibit structural variation at the 1-position as described below, it is preferred that the activated coupling group be present at one or other of positions 2 to 11 inclusive, thus leaving the residue at the 1-position intact, preferably "unmasked" by the carrier, in the immunogenic conjugate subsequently obtained, and hence free to elicit specific antibody response. Generally it is appropriate if the activated coupling group is at the 2-position or at any of the positions 3, 5 to 8 or 10, especially 5 to 8 inclusive, whereby the 2- and 8-positions are particularly favoured.

In the case of Cyclosporine major metabolic conversions occurring in man are:

I Terminal hydroxylation of -MeLeu$^9$- to give the residue of formula E

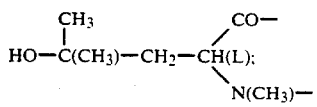

II Terminal hydroxylation of -MeBmt$^1$- to give the residue of formula F

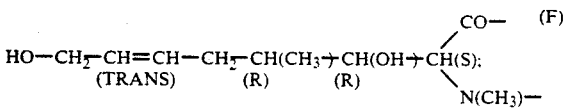

III Des-N-methylation of -MeLeu$^4$- to give -Leu-;
IV Terminal hydroxylation of -MeLeu$^4$- to give the residue of formula E above;
V Terminal hydroxylation of -MeLeu$^6$- to give the residue of formula E above;
VI Terminal hydroxylation and ring-closure in -MeBmt$^1$- to give the residue of formula G

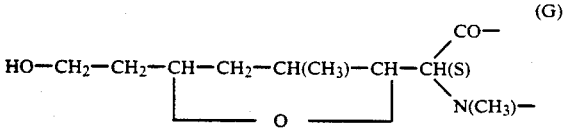

Thus known metabolites of Cyclosporine (identified as Cyclosporine 1, Cyclosporine 8 etc . . . ) exhibit the following metabolic variations.

Cyclosporine 1:I. Cyclosporine 8:I+II. Cyclosporine 9:I+III+V. Cyclosporine 10:I+IV. Cyclosporine 16:I+V. Cyclosporine 17:II. Cyclosporine 18:VI. Cyclosporine 21:III.

[See G. Maurer et al, "Drug Metab. Disposit" 12, 120–126 (1984)].

Accordingly, for the preparation of monoclonal antibodies capable of distinguishing between Cyclosporine and metabolites thereof in man, it will be appropriate that the activated coupling group in the cyclosporin employed for immunogenic conjugate formation, be situated in a position other than the 1-, 4-, 6- or 9-position, and, in so far as Cyclosporine 17 and 18 represent major metabolites, at least in a position other than the 1-position. Thus again in the particular case of Cyclosporine, the 2- and 8-position are especially favoured.

Cyclosporins having an activated coupling group as described above may be prepared e.g. either:

i) by activation of an appropriate pre-existing precursor group (i.e. coupling group in non-activated form), e.g. conversion of the carboxy group of a cyclosporin having a carboxy-substituted α-amino acid residue (i.e. α-amino acid residue having a side chain at the α-carbon atom comprising or bearing a carboxy group), e.g. at the 2- or 8-position, into an activated carboxy group, by reaction with a carboxy activating agent; or ii) by acylation or etherification of a cyclosporin having an amino- or hydroxy-substituted α-amino acid residue (i.e. α-amino acid residue having a side chain at the α-carbon atom comprising or bearing a hydroxy or amino group), e.g. hydroxy-substituted α-amino acid residue at the 2-position or amino- or hydroxy-substituted α-amino acid residue at the 8-position, with an acylating or alkylating agent bearing an activated coupling group.

Process step i) above may be carried out in accordance with standard techniques known in the art, e.g. for the activation of carboxy groups by reaction with a regular carboxy activating agent such as o- or p-nitrophenol, 1-hydroxy-benztriazole, pentafluorophenol or N-hydroxy-succinimide. Reaction is suitably carried out in the presence of a condensing agent such as EDCI.

Process step ii) may also be carried out in accordance with essentially conventional techniques. Thus amino or hydroxy groups may be suitably acylated by reaction with a derivative of a carboxylic acid in which the carboxy group is activated and which additionally bears an activated coupling group which is non-reactive with amino or hydroxy as the case may be, for example N-[(2-pyridyl)dithio-propion-1-yl]-succinimide, [the (2-pyridyl)dithio moiety providing the activated coupling group (non reactive, in this instance, with both amino and hydroxy groups) and the -COO-succinimido moiety the activated carboxy group for effecting acylation]. Reaction is suitably performed in an inert solvent or diluent such as dichloromethane at e.g. ambient temperature. Alternatively hydroxy groups may be etherified, e.g. to introduce an epoxy bearing moiety of formula

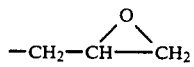

[the epoxy moiety providing the activated coupling group] employing any of the various agents known in the art for such purpose, such as epichlorhydrin or epibromhydrin, e.g. in accordance with the general procedures described by Laumen et al. Loc. cit..

Cyclosporin starting materials for process step i) above may be prepared analogously to process step ii), e.g. for the production of a cyclosporin having a carboxy-substituted α-amino acid residue, e.g. at the 2- or 8-position:

iii) by reaction of a cyclosporin having an amino- or hydroxy-substituted α-amino acid residue, e.g. hydroxy-substituted α-amino acid residue at the 2-position or amino- or hydroxy-substituted α-amino acid residue at the 8-position, either a) with a dicarboxylic acid in which one of the carboxy groups present is in protected form, or b) with a dicarboxylic acid anhydride e.g. succinic anhydride, reaction in case a) being followed by deprotection of the carboxy group in the product cyclosporin.

Reaction step iii) may also be carried out employing essentially conventional procedures, e.g. in the presence of an acid binding agent such as 4-dimethylaminopyridine, in an inert organic solvent or diluent, at ambient or slightly elevated temperature. Where carboxy protecting groups are employed as in variant a) these may be entirely conventional and removed by entirely conventional technique.

Cyclosporin starting materials for process steps ii) and iii) a hydroxy-substituted α-amino acid residue include the known cyclosporins: [Thr]²-Cyclosporine and [(D)Ser]⁸-Cyclosporine, the latter being disclosed and claimed e.g. in European Patent No. 0 056 782, together with processes for its production in accordance with the general techniques of the total-synthetic method for the production of cyclosporins referred to above, or by fermentation technique. Other cyclosporins having a hydroxy-substituted α-amino acid residue, e.g. in the 8-position, may be prepared or obtained analogously and various further such Cyclosporins including [(D)Thr]⁸-Cyclosporine, [Nva]²-[(D)Ser]⁸-Cyclosporine, and [Thr]²-[(D)Ser]⁸-Cyclosporine have been described and claimed in U.S. patent application Ser. No. 713 259 (filed 19 Mar., 1985)=W. German Appn. No. P 3 509 809.0 (filed 19 Mar., 1985)=French Appn. No. 8 404 172 (filed 19 Mar., 1985)≡Australian Appn. No. 40 272/85 (filed 22 Mar., 1985)≡UK Appn. No. 8 507 270 (filed 20 Mar., 1985)≡New Zealand Appn. No. 211 526 (filed 21 Mar., 1985)≡South African Appn. No. 85/2195 (filed 22 Mar., 1985).

Preferred cyclosporins having an amino-substituted α-amino acid residue are those wherein the said amino acid residue is at the 8-position, cyclosporins wherein the residue at the 8-position is -(D)Lys- being especially preferred. Such cyclosporins may also be prepared in accordance with the general techniques of the total-synthetic method for the production of cyclosporins developed by R. Wenger, e.g.

iv) by deprotection of a cyclosporin having an amino-substituted α-amino acid residue at the 8-position said cyclosporin being in protected form, e.g. by deprotection of a cyclosporin wherein the residue at the 8-position is -(D)Lys- in N-ε-protected form; or v) cyclising a straight chain undecapeptide having the sequence of the product cyclosporin, said undecapeptide being in free or protected form, e.g. undecapeptide comprising a -(D)Lys-residue in free or N-ε-protected form at the position corresponding to the 8-position of the product cyclosporin, and when required carrying out precess step iv).

Process steps iv) and v) may in particular be carried out in accordance with the general procedure hereinafter illustrated in example 1.

As will be appreciated from the description of process steps i), ii) and iii) above, the products of steps i) or ii) will generally comprise cyclosporins having an acylamino-, acyloxy- or alkoxy-substituted α-amino acid residue (i.e. α-amino acid residue having a side chain at the α-carbon atom comprising or bearing an acylamino-, acyloxy- or alkoxy- group), e.g. cyclosporin having an acyloxy- or alkoxy-substituted α-amino acid residue at the 2-position or acylamino-, acyloxy- or alkoxy-substituted α-amino acid residue at the 8-position, in which the activated coupling group is present on the acyl/alkyl moiety.

This may be more readily appreciated by reference to the following reaction schemes, illustrating the production of particular groups of cyclosporins in accordance with the general methods of process steps i) to v) above:

In the following formula Ia to Id, IIa to IId and III. C represents the sequence —Sar—MeLeu—Val—MeLeu—Ala—, and
  3    4    5    6    7

E represents the sequence —MeLeu—MeLeu—MeVal—.
                            9      10     11

Reaction step i)

a) ⌐—A¹—B$_a$¹—C—D¹—E—⌐    (Ia)

in which

A¹ = —MeBMt—,
B$_a$¹ = —(O-acyl)-Thr— in which the acyl moiety bears a coupling group in non-activated form, for example a free carboxy group, e.g.
—(O-hydroxysuccinyl)-Thr—, and
D¹ = —(D)Ala:

Activation, e.g. by reaction with a carboxy activating agent suitably in the presence of a coupling agent such as EDCI:

↓

⌐—A¹—B$_b$¹—C—D¹—E—⌐    (IIa)

in which
A¹ and D¹ have the meanings given above, and
B$_b$¹ = —(O-acyl)-Thr — in which the acyl moiety bears an activated coupling group, for example an activated carboxy group, e.g.
—(O-acyl)-Thr— in which the acyl moiety has the formula ZO—CO—(CH$_2$)$_2$—CO— in which Z is a carboxy activating group.

b) ⌐—A²—B²—C—D$_a$²—E—⌐    (Ib)

in which

A² = —MeBmt— B² = -αAbu— or —Nva—, or
A² = -dihydro-MeBmt—, and B² = —Val— and
D$_a$² = an acylamino substituted (D)α-amino acid residue, e.g. —(N-ε-acyl)-(D)Lys—, in which the acyl moiety bears a coupling group in non-activated form, for example a free carboxy group, e.g.
—(N-ε-hydroxy-succinyl)-(D)Lys—:

Activation, e.g. by reaction with a carboxy activating agent, e.g. N-hydroxy succinimide, suitably in the presence of a coupling agent such as ECDI:

↓

⌐—A²—B²—C—D$_b$²—E—⌐    (IIb)

in which

A² and B² have the meanings given above and
D$_b$² = an acylamino substituted (D)α-amino acid residue, e.g. —(N-ε-acyl)-(D)Lys—, in which the acyl moiety bears an activated coupling group, for example an activated carboxy group, e.g.
—(N-ε-acyl)-(D)Lys— in which the acyl moiety has the formula
ZO—CO—(CH$_2$)$_2$—CO—
in which Z has the meaning given above Reaction step ii)

-continued a) $\boxed{-A^1-B_a{}^3-C-D^1-E-}$ (Ic)

in which
A$^1$ and D$^1$ have the meanings given above, and
B$_a{}^3$ = —Thr—:

| O-alkylation to introduce an alkyl moiety
| bearing an activated coupling group, e.g.
| epoxy group, e.g. by reaction with
| epichlorhydrin or epibromohydrin:

$\boxed{-A^1-B_b{}^3-C-D^1-E-}$ (IIc)

in which
A$^1$ and D$^1$ have the meanings given above, and
B$_b{}^3$ = —(O-alkyl)-Thr— in which the alkyl
moiety bears an activated coupling group, for
example an epoxy group, e.g.
—(O-epoxymethyl)-Thr—.

b) $\boxed{-A^2-B^2-C-D_a{}^3-E-}$ (Id)

in which
A$^2$ and B$^2$ have the meanings given above and
D$_a{}^3$ = an amino substituted (D)α-amino acid
residue, e.g. —(D)Lys—:

| N-ε-acylation employing an acylating
| agent bearing an activating coupling group
| non-reactive with —NH$_2$, e.g. an acylating agent
| of formula ZO—CO—(CH$_2$)$_2$—Y wherein Z
| has the meaning given above and Y is an
| activated coupling group non-reactive with —NH$_2$,
| e.g. a 2-pyridyl-dithio group:

$\boxed{-A^2-B^2-C-D_b{}^3-E-}$ (IId)

in which
A$^2$ and B$^2$ have the meanings given above, and
D$_b{}^3$ = an acylamino substituted (D)α-amino
acid residue, e.g. —N(-ε-acyl)-(D)Lys—,
in which the acyl moiety bears an activated
coupling residue, e.g.
—[N-ε-(3-(2-pyridyl)dithio-
propion-1-yl)]-(D)Lys—.

Reaction step iii)

a) A cyclosporin of formula Ic as defined above:

| Acylation, e.g. by reaction with
| with succinic anhydride:

A cyclosporin of formula Ia as defined above.

b) A cyclosporin of formula Id as defined above:

| Acylation, e.g. by reaction with
| succinic anhydride:

A cyclosporin of formula Ib as defined above.

Reaction step iv)

$\boxed{-A^2-B^2-C-D_a{}^4-E-}$ (Ie)

in which
A$^2$ and B$^2$ have the meanings given above and
D$_a{}^4$ = an amino substituted (D)α-amino
acid residue, e.g. -(D)Lys—, in protected form:

| Deprotection

A cyclosporin of formula Id as defined above.

Reaction step v)

H—D$_a{}^5$—E—A$^1$—B$^2$—C—OH (III)

in which
A$^2$ and B$^2$ have the meanings given above and

D$_a{}^5$ = an amino substituted (D) α-amino acid
residue, e.g. -(D)Lys—, in
free or —N-ε-protected form:

| Cyclisation in accordance with the method
| of R. Wenger:
↓

A Cyclosporin of formula Id or Ie as defined above.

It may at this point be noted that the hydroxy group at the 3'-position in -MeBmt- and -dihydro-MeBmt- is of relatively low reactivity. Thus where processes described above involve reaction of cyclosporins having a hydroxy substituted α-amino acid residue at any one of positions 2 to 11, e.g., -Thr- in the 2-position, reaction with the hydroxy group of said residue will be in preference to reaction with the hydroxy group in -MeBmt- or -dihydro-MeBmt-, unwanted side reaction with the latter thus being readily avoidable.

In the formulae Ib, IIb, Id, IId, Ie and III above, A$^2$ and B$^2$ preferably represent -MeBmt- and -αAbu- respectively.

Whenever throughout the whole of the foregoing description, cyclosporins are referred to as having a specified residue at the 8-position, but the configuration of said residue is not recited, the (D)-configuration is preferred.

Cyclosporins having an activated coupling group described above as well as cyclosporins having an amino-substituted α-amino acid residue at the 8-position in which the amino substituent is in free or protected form, or is otherwise derivatised, e.g. acylated are novel and comprise a part of the present invention. The present invention accordingly provides:

1.1 A cyclosporin having an α-amino acid residue bearing an activated coupling group.

1.2 A cyclosporin according to 1.1 wherein the said α-amino acid residue is present at one of positions 2 through 11 inclusive.

1.3 A cyclosporin according to 1.2 wherein the said α-amino acid residue comprises an acylamino-, acyloxy- or alkoxy-substituted α-amino acid residue in which, the activated coupling group is present on the acylamino-, acyloxy- or alkoxy substituent.

1.4 A cyclosporin according to any one of 1.1 to 1.3 wherein the activated coupling group is an activated ester, activated dithio, or epoxy group.

1.5 A cyclosporin according to 1.3 wherein the said α-amino acid residue comprises: an acylamino substituted α-amino acid residue, wherein the acylamino substituent is substituted in the acyl moiety thereof by an activated carboxy or activated dithio group; an acyloxy substituted α-amino acid residue, wherein the acyloxy substituent is substituted in the acyl moiety thereof by an activated carboxy group; or an alkoxy substituted α-amino acid residue, wherein the alkoxy substituent is substituted by an epoxy group.

1.6 A cyclosporin according to any one of 1.3 to 1.5 wherein the said α-amino acid residue is an (O-acyl)-threonyl residue at the 2-position.

1.7 A cyclosporin according to 1.6 wherein the acyl moiety has the formula ZO—CO—CH$_2$—CH$_2$—CO— wherein Z is a carboxy activating group.

1.8 A cyclosporin according to 1.2 wherein the said α-amino acid residue is present at the 5-, 6-, 7- or 8-position.

1.9 A cyclosporin according to 1.8 wherein the said α-amino acid residue is a (D)α-amino acid residue in the 8-position.

1.10 A cyclosporin according to 1.9 wherein the said α-amino acid residue is an acylamino substituted (D)α-amino acid residue in which the activated coupling group is present on the acylamino substituent.

1.11 A cyclosporin according to 1.10 wherein the activated coupling group is an activated carboxy or activated dithio group.

1.12 A cyclosporin having an amino substituted (D)α-amino acid residue at the 8-position the amino substituent being in free or protected form.

1.13 A cyclosporin having an acylamino substituted (D)α-amino acid residue at the 8-position wherein the acylamino substituent is substituted in the acyl moiety thereof by a free carboxy group.

1.14 A cyclosporin according to any one of 1.10 to 1.13 of formula

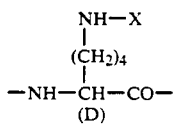

wherein X is hydrogen, an amino protecting group or an acyl group substituted by a free carboxy group or an activated coupling group, for example an activated carboxy or dithio group, e.g. an acyl group of formula

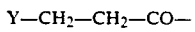

wherein Y is carboxy, an activated carboxy group or an activated dithio group.

1.15 A cyclosporin of formula IIa, Ib, IIb, IIc, Id, IId or Ie as hereinbefore defined.

As hereinbefore discussed it has, in accordance with the present invention, now surprisingly been found that immunogenic conjugates comprising a carrier and a cyclosporin coupled by the agency of an activated coupling group, in particular, obtained employing cyclosporins having an activated coupling group as described above, e.g. as defined under 1.1 to 1.11, 1.14 or 1.15, enable, for the first time, the production of monoclonal antibodies capable of distinguishing between cyclosporins and metabolites thereof. Thus immunogenic conjugates comprising the reaction products of such cyclosporins as aforesaid as hapten component are capable of eliciting an antibody response in animals challenged, e.g. inoculated therewith, such that antibody producing cells, e.g. spleen or lymph-node cells, subsequently recoverable therefrom may be used for the preparation of hybridoma lines providing monoclonal antibodies capable of distinguishing between therapeutically administered cyclosporins, e.g. Cyclosporine, and metabolites thereof, in particular metabolites thereof in man, e.g. Cyclosporine 17 and Cyclosporine 18. Such antigenic conjugates being hitherto unknown, the present invention further provides:

2.1 An immunogenic conjugate comprising a carrier coupled to a cyclosporin by the agency of an activated coupling group, for example comprising a carrier coupled to a cyclosporin having an α-amino acid residue bearing an activated coupling group, e.g. as hereinbefore described, in particular a cyclosporin as hereinbefore defined under any one of 1.1 to 1.11, 1.14 or 1.15 (formulae IIa, IIb, IIc or IId) above.

2.2 An immunogenic conjugate obtained or obtainable by coupling of a cyclosporin having an α-amino acid residue bearing an activated coupling group, e.g. as hereinbefore described, in particular a cyclosporin as hereinbefore defined under any one of 1.1 to 1.11, 1.14 or 1.15 (formulae IIa, IIb, IIc or IId) above.

2.3 An immunogenic conjugate, e.g. as defined under 2.1 or 2.2, capable of use in the production of a monoclonal antibody capable of distinguishing between a cyclosporin and a metabolite thereof, e.g. a monoclonal antibody as hereinafter described and, in particular, as hereinafter defined under any one of 3.1 to 3.10 below.

Suitable carriers for the immunogenic conjugates of the invention include any of those known and commonly employed in the art in particular high molecular weight polypeptides, especially proteins such as serum albumins, e.g. bovine serum albumin and chicken ovalbumin, immunoglobulins, in particular of the class IgG such as chicken or guinea pig IgG and synthetic polymers such as polyglutamic acid.

In addition the present invention provides a process for the production of an immunogenic conjugate as defined above, which process comprises:

vi) Coupling a carrier, e.g. as hereinabove described, bearing an activated coupling group with a cyclosporin having an α-amino acid residue bearing an appropriate co-reactive, e.g. hydroxy or amino, group, e.g. with [Thr]²-Cyclosporine or [(D)Lys]⁸-Cyclosporine, or coupling a carrier, e.g. as hereinabove described, with a cyclosporin having an α-amino acid residue bearing an activated coupling group, e.g. as hereinbefore described, in particular a cyclosporin as hereinbefore defined under any one of 1.1 to 1.11, 1.14 or 1.15 (formulae IIa, IIb, IIc or IId) above.

The above process step is carried out by direct reaction of the cyclosporin component, i.e. without use of a coupling agent. Reaction is suitably effected by addition of the cyclosporin component dissolved in an appropriate inert diluent or carrier such as dimethyl formamide to a buffered preparation of the carrier, e.g. carrier protein, e.g. solution or supension in bicarbonate buffer, at ambient temperature. The obtained immunogenic conjugate is suitably purified by dialysis, e.g. against phosphate buffered saline.

The above described immunogenic conjugates, e.g. as defined under 2.1 to 2.3, may be employed to produce monoclonal antibodies by essentially standard techniques, e.g. via a stepwise procedure comprising: a) administration of an immunogenic conjugate, e.g. as defined under any one of 2.1 to 2.3 above, to an appropriate animal species; b) recovery of antibody producing, e.g. spleen or lymph-node, cells sensibilised to the immunogenic conjugate; c) immortalization of recovered cells, e.g. by fusion with an appropriate myeloma cell line to produce hybridoma cell lines; and d) selection of an immortalized cell, e.g. hybridoma line , producing monoclonal antibodies as required.

Step a) is suitably carried out using rats or mice, e.g. ♀ Balb/c mice as recipient, and administration of the immunogenic conjugate by s.c. or i.p. injection in an amount of from ca. 50 to 200, e.g. ca. 100 μg followed by booster injections, i.p., s.c. or i.m., 14 to 21 days later. Mice showing high-titred antisera of appropriate isotype distribution, e.g. as determined by regular RIA and/or ELISA technique, are given further booster injections e.g. in accordance with the specific procedures hereinafter described in example 9, and antibody producing, e.g. spleen cells, collected [step b)]. Step c) may be performed in accordance with any of the techniques practiced in the art, e.g. using the method described by S. Fazekas et al., "J. Immunol. Methods" 35, 1–32 (1980), a preferred myeloma line being a mouse (Balb/C) line. In step d), growing myeloma lines are screened for antibody production against a cyclosporin, e.g. in a regular RIA system using a radiolabelled derivative thereof or in a regular ELISA system, e.g. as hereinafter described in example 9.

By application of the above procedures using the particular immunogenic conjugates of the present invention, it is possible to obtain monoclonal antibodies which exhibit a degree of specificity such that they are capable of distinguishing between individual cyclosporins differing from one another in only minor structural elements, e.g. presence of a single hydroxy group in place of a hydrogen atom. More importantly the present invention makes it possible, for the first time, to obtain monoclonal antibodies capable of distinguishing between cyclosporins, e.g. Cyclosporine, and metabolites thereof, in particular metabolites thereof in man. Thus monoclonal antibodies obtainable in accordance with the methods of the invention are found to be reactive with cyclosporins, e.g. Cyclosporine, while exhibiting relatively low cross-reactivity with metabolites thereof. Moreover employing immunogenic conjugates in accordance with the invention, e.g. as defined under 2.1 to 2.3 above, in which the cyclosporin hapten component corresponds to a selected "target" cyclosporin, the present invention enables the obtention of monoclonal antibodies capable of distinguishing between the "target" cyclosporin and structurally closely related metabolites, e.g. human metabolites, thereof. Thus starting from immunogenic conjugates obtained by coupling of a carrier with a cyclosporin having an activated coupling group at the 2-position, e.g. as defined under 1.6 above, and in which the α-amino acid residues at the remaining positions 1 and 3 to 11 are the same as those in Cyclosporine, it is possible to prepare monoclonal antibodies reactive with Cyclosporine as "target" cyclosporin in preference to metabolites thereof in man, e.g. Cyclosporines 1, 8, 9, 10, 16, 17, 18 and/or 21, in particular 17 and/or 18 and especially 17. Similarly, starting from immunogenic conjugates obtained by coupling of a carrier with a cyclosporin having an activated coupling group at the 5-, 6-, 7- or 8-position, e.g. as defined under 1.8 above, in particular the 8-position, e.g. as defined under any one of 1.9, 1.11, 1.14 or 1.15 (formulae IIb or IId) above, and in which the residues at the remaining positions, e.g. 1 to 7 and 9 to 11, correspond to those in Cyclosporine, dihydro-[Val]$^2$-Cyclosporine or [Nva]$^2$-Cyclosporine, monoclonal antibodies may be prepared reactive with Cyclosporine, dihydro-[Val]$^2$-Cyclosporine or [Nva]$^2$-Cyclosporine as "target" cyclosporin, in preference to metabolites thereof, e.g. metabolites thereof in man, such as, in the case of Cyclosporine, those recited immediately above.

Monoclonal antibodies obtainable in accordance with the methods of the invention are, in particular, capable of distinguishing between "target" cyclosporins and metabolites thereof exhibiting structural transformation of the α-amino acid residue at the 1-position, e.g. metabolites which differ from the non-metabolised cyclosporin from which they are derived by substitutional or other chemical modification of the -MeBmt- or -dihydro-MeBmt- residue at the 1-position, in particular exhibiting structural transformation at a terminal position in the residue at the 1-position, e.g. comprising hydroxylation at of the terminal (C$^9$) -MeBmt- methyl group, as in the case of monoclonal antibodies described in the accompanying example 9, which are reactive with Cyclosporine while having relatively low cross-reactivity with its metabolite Cyclosporine 17. In so far as such metabolic transformation of cyclosporin is of especial significance, e.g. as characteristic of major metabolites in man, as in the case of Cyclosporins 17 and 18, ability of monoclonal antibodies obtainable in accordance with the methods of the invention to distinguish between cyclosporins and metabolites thereof exhibiting such transformation is in particular to be noted.

Cross-reactivity with metabolites, e.g. as described above, is preferably ca. 5% or less, more preferably ca. 3% or less, more preferably ca. 2% or less, of reactivity with the non-metabolised cyclosporin, e.g. as measure by RIA or ELISA, e.g. competitive ELISA, technique, suitably employing a buffer e.g. of ca. pH 6 to 8, in particular 7 to 8, and appropriately also containing a minor amount, e.g. 0.01 to 0.1% e.g. 0.01 to 0.05%, of a non-ionic surfactant or tenside such as Tween, for example phosphate buffered saline at pH 7.5 and containing 0.03% surfactant, e.g. Tween 20. Thus monoclonal antibodies obtainable in accordance with the methods of the invention and reactive with Cyclosporine exhibit a distinction in IC$_{50}$ ratio for Cyclosporine 17 as compared with Cyclosporine, measured by competitive ELISA technique under conditions as set forth above of the order of 35 fold or greater.

Monoclonal antibodies obtainable in accordance with the methods of the invention are also characterised by high affinity for the "target" cyclosporin, e.g. Cyclosporine. Thus preferred monoclonal antibodies in accordance with the invention will exhibit an affinity constant [equilibrium dissociation constant] in respect of the "target" cyclosporin, e.g. Cyclosporine, of the order of $10^{-9}$ mol/L or less, preferably $10^{-10}$ mol/L or less, e.g. at normal RIA temperatures (ca. 4° to 37° C.) as determined by standard methods, e.g. in accordance with the method described by Müller et al., Methods in Enzymology, 92, 589–601 (1983).

The present invention further permits the ready obtention of monoclonal antibodies of the class IgG, e.g. of the sub-class IgG$_1$. In so far as such antibodies are especially suited to use in diagnostic/assay kits, e.g. as described below, these are preferred.

Monoclonal antibodies as described above, as well as hybridoma lines producing them are entirely novel and, as will be appreciated from the foregoing description of their general and specific properties, well adapted for use in diagnostic/assay kit systems, e.g. for monitoring of cyclosporin drug plasma-blood levels in patients receiving cyclosporin therapy. The present invention accordingly also provides:

3.1 A monoclonal antibody capable of distinguishing between a cyclosporin, e.g. a predetermined cyclosporin, and a metabolite thereof, in particular at least one metabolite thereof in man, especially at least one major metabolite thereof in man.

3.2 A monoclonal antibody according to 3.1 reactive with a cyclosporin, e.g. a predetermined cyclosporin, and exhibiting relatively low cross-reactivity with a metabolite thereof, in particular at least one metabolite thereof in man, especially at least one major metabolite thereof in man.

3.3 A monoclonal antibody according to 3.1 or 3.2 wherein the cyclosporin is Cyclosporine, dihydro-[Val]$^2$-Cyclosporine or [Nva]$^2$-Cyclosporine, especially Cyclosporine.

3.4 A monoclonal antibody according to any one of 3.1 to 3.3 wherein the metabolite is a metabolite exhibiting structural transformation of the α-amino acid residue at the 1-position, in particular at a terminal position on the residue at the 1-position, e.g. exhibiting terminal hydroxylation of the α-amino acid residue -MeBmt- at the 1-position.

3.5 A monoclonal antibody according to 3.4 wherein the cyclosporin is Cyclosporine and the metabolite is Cyclosporin 1, 8, 9, 10, 16, 17, 18 or 21, especially Cyclosporine 17 or 18, most especially Cyclosporine 17.

3.6 A monoclonal antibody according to any one of 3.2 to 3.5 wherein cross reactivity with the metabolite is of the order of ca. 5% or less, preferably 3% or less, more preferably 2% or less, e.g. as measured by RIA or ELISA technique, for example under conditions as hereinbefore set forth.

3.7 A monoclonal antibody according to any one of 3.1 to 3.6 wherein the affinity constant with respect to the (predetermined) cyclosporin, e.g. Cyclosporine, is of the order of $10^{-9}$ mol/liter or less, preferably $10^{-10}$ mol/liter or less, e.g. as measured under conditions as hereinbefore set forth.

3.8 A monoclonal antibody according to any one of 3.1 to 3.7 of the class IgG.

3.9 A monoclonal antibody, e.g. according to any one of 3.1 to 3.8, obtained or obtainable by:
a) coupling of a cyclosporin having an α-amino acid residue bearing an activated coupling group, e.g. as hereinbefore described, in particular as hereinbefore defined under any one of 1.1 to 1.11, 1.14 or 1.15 (formulae IIa, IIb, IIc or IId) above, to a carrier to obtain an immunogenic conjugate;
b) administration of said immunogenic conjugate to an appropriate animal species to effect immunogenic challenge, and recovery of antibody producing cells sensitised to said conjugate;
c) immortalisation of said antibody producing cells, e.g. by fusion with an appropriate myeloma cell line; and
d) recovery of monoclonal antibody from a selected immortalised cell line, e.g. hybridoma cell line, thus established.

3.10 A monoclonal antibody, e.g. according to any one of 3.1 to 3.8 obtained or obtainable by:
a) recovery of antibody producing cells sensitised to an immunogenic conjugate according to any one of 2.1 to 2.3 above;
b) immortalisation of said antibody producing cells, e.g. by fusion with an appropriate myeloma cell line, and
c) recovery of the required monoclonal antibody from a selected immortalised cell line, e.g. hybridoma cell line, thus established.

4.1 A hybridoma cell line producing a monoclonal antibody according to any one of 3.1 to 3.8 above.

4.2 A hybridoma cell line obtained or obtainable in accordance with steps a) to c) of 3.9 above or steps a) and b) of 3.10 above.

As will be appreciated, monoclonal antibodies in accordance with the invention may distinguish between any given cyclosporin, e.g. Cyclosporine, and a plurality of its metabolites, e.g. exhibit low-cross reactivity with respect to more than one of its metabolites.

In addition to the foregoing the present invention also provides:

vii) A method for the production of a monoclonal antibody as defined under any one of 3.1 to 3.8 above, which method comprises culturing a hybridoma cell line producing such antibody and recovering the antibody thus produced; and viii) A method for the production of a hybridoma cell line producing a monoclonal antibody as defined under any one of 3.1 to 3.8 above, which method comprises immortalizing an antibody producing cell, e.g. spleen or lymph-node cell, producing such antibody, e.g. by fusion with an appropriate myeloma cell line.

The above process steps may be performed in accordance with now standard techniques, e.g. as hereinabove described, or as described in the accompanying examples, preferred myeloma cell lines for use in process viii) being a mouse (Balb/C) myeloma cell line.

In accordance with a yet further aspect of the present invention it has also surprisingly been found that cyclosporins having a -(D)Lys- residue at the 8-position, i.e. as defined under 1.14 or 1.15 (formula Id) above, as well as derivatives in which the N-ε-atom thereof is further derivatised, exhibit e.g. cell binding characteristics which parallel those of the corresponding "parent" cyclosporin (e.g. the corresponding cyclosporin having -(D)Ala- at the 8-position) to a surprising and remarkable degree. This finding is of especial significance since the N-ε-nitrogen atom of -(D)Lys- provides an ideal position at which labelling may be effected, e.g. at which label or tracer groups may be introduced. Such labelled cyclosporins provide a further key tool for study of the mechanism of action of "parent" cyclosporins (e g. in the case of [(D)Lys]$^8$-Cyclosporine of Cyclosporine) and/or for identifying binding sites of the "parent" cyclosporin, e.g. in in vitro tissue culture preparations. Thus radioactively labelled derivatives, e.g. $^{125}$I labelled derivatives, are useful for rapid autoradiography of tissues, e.g. as in kidney micro-autoradiography.

In addition labelled, e.g. radioactively or fluorescently labelled, derivatives obtainable from cyclosporins having a -(D)Lys- residue at the 8-position provide ideal components for use e.g. in RIA and FIA diagnostic kits. [(D)Lys]$^8$-cyclosporins thus provide a means for the ready obtention of labelled analogues of the "parent" cyclosporin having equivalent binding properties, e.g. in relation to monoclonal antibodies to the parent cyclosporin, e.g. as obtained in accordance with the present invention or as hereinabove defined, and hence emminently useful as diagnostic/assay kit component or co-component.

Accordingly the present invention also provides:

5.1 A labelled derivative of a cyclosporin wherein the residue at the 8-position is -(D)Lys-; in particular 5.2 A labelled derivative of a cyclosporin of formula Id as defined above.

By the term "labelled derivative" as used herein is meant a derivative bearing a tracer or marker atom or group, e.g. enabling or facilitating quantitative assay or location of said derivative. Such derivatives include derivatives, e.g. wherein one or more atoms of the -(D)Lys- residue functions as a tracer or marker atom, e.g. radioactive atom, as well as derivatives wherein a tracer or marker group is attached to the N-ε-atom of the -(D)Lys- residue either by direct linkage of the tracer or marker group to said N-ε-atom or by linkage of the tracer or marker group to said N-ε-atom via an intervening linking moiety. Examples of labelled derivatives include radioactively labelled derivatives, fluorescent and chemiluminescent derivatives and derivatives suitable for photoaffinity labelling, i.e. provided with a substituent which will react with a protein to which the cyclosporin is bound on illumination. Radioactively labelled derivatives as aforesaid include derivatives wherein the N-ε-atom of the -(D)Lys- residue at the 8-position attaches to e.g. an $^{125}I$ labelled p-OH-phenyl-propionyl residue. Fluorescent and chemiluminescent derivatives as aforesaid include derivatives wherein the N-ε-atom of the -(D)Lys- residue at the 8-position attaches to a fluorescent group, such as a dansyl or rhodamine group, or chemiluminescent group such as an acridinium ester group, e.g. as described in Clin. Chem. 29, 8, pp 1474–1479 (1983). A particular group of cyclosporins as defined under 5.1 and 5.2 above are accordingly 5.3 those wherein the residue at the 8-position is a residue of formula

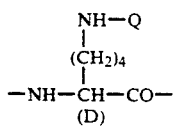

wherein Q is or comprises a tracer or marker group, in particular radioactively labelled, fluorescent or chemiluminescent group, e.g. as specifically described above.

Labelled derivatives as aforesaid may be prepared analogously to process steps iv) and v) above, e.g. employing starting materials in which the -(D)Lys- residue at the 8-position is pre-labelled. Alternatively they may be prepared by introduction of an appropriate labelling substituent, e.g. at the N-ε-atom of the -(D)Lys- residue at the 8-position. Thus fluorescently labelled derivatives may be prepared by coupling of a fluorescent moiety to the N-ε-atom e.g. by N-ε-dansylation. Similarly radioactively labelled derivatives may be prepared by coupling of a radioactively labelled substituent, e.g. $^{125}I$ labelled p-OH-phenyl-propionyl, to the N-ε-atom. In the latter case the substituent may either be in labelled form prior to introduction or may be labelled subsequent to introduction. For example the N-ε-atom of the lysine residue in the 8-position may either be reacted directly with $^{125}I$-labelled p-OH-phenyl-propionic acid or with unlabelled p-OH-phenyl-propionic acid and the obtained N-ε-amide subsequently labelled in the p-OH-phenyl moiety with $^{125}I$. Coupling may be effected in accordance with standard techniques known in the art for example by reaction with p-OH-phenyl-propionic acid (labelled or unlabelled) in the form of its N-hydroxy-succinimide ester.

$^{125}I$ labelled-p-OH-phenyl-propionic acid may itself be prepared by the chloramine T-method [Hunter and Greenwood, Nature, 194, 495 (1962)]. Where labelling is effected subsequent to coupling this may be carried out using the chloramin T-method or the iodogen-method [Good, J.Clin.-Chem.Clin.Biochem., 19, 1051 (1981)]. Derivatives of the cyclosporins of the invention which are susceptible to labelling, e.g. as described above, for example derivatives wherein the N-ε-atom of -(D)Lys- at the 8-position is substituted by a group, such as p-OH-phenyl-propionyl, susceptible to 125iodination, are immediate precursors of the labelled derivatives of the invention and are also to be understood as being within the purview of the present invention. In accordance with the foregoing the present invention also provides:

ix) A process for the production of a labelled derivative as defined under any one of 5.1 to 5.3 above, in free or protected form, which process comprises labelling the corresponding unlabelled free or protected cyclosporin, e.g. introducing a labelling substituent, for example as hereinbefore described, at the N-ε-atom of the -(D)Lys- residue at the 8-position thereof, and when required carrying out process step iv) above.

It may at this point additionally be noted, that the cyclosporins having a free amino group as defined under 1.12 above, for example the compound L(D)Lys]$^8$-Cyclosporine, also possess pharmaceutical, in particular immunosuppressive, anti-inflammatory and anti-parasitic (e.g. anti-malarial and anti-coccidiomycotic), activity, as can be demonstrated in standard in vivo and in vitro tests, for example in the various test methods described in European Patent No. 0 056 782.

In accordance with a yet further aspect of the present invention it has been found that immunogenic conjugates in which the carrier molecule is coupled to a cyclosporin as hapten via the residue at the 5-, 6-, 7- or 8-position, in particular the 8-position, including such conjugates as defined under 2.1 to 2.3 above, as well as conjugates obtained by coupling of a cyclosporin bearing an amino acid having a reactive group at any one of these positions other than an activated coupling group to a carrier by means of a coupling agent, are capable of generating regular polyclonal antisera of higher specificity than hitherto obtainable e.g. employing conjugates obtained by coupling of a carrier to -(Thr)$^2$- in (Thr)$^2$-Cyclosporine.

(By the term "reactive group" as used above is to be understood any group which permits or enables coupling with a carrier, e.g. polypeptide or other appropriate macromolecule. Generically the term thus embraces activated coupling groups as hereinbefore defined as well as other groups capable of reaction, e.g. free amino, carboxy or hydroxy groups).

Immunogenic conjugates comprising a cyclosporin as hapten, linked to a carrier via the α-amino acid residue at the 5-, 6-, 7- or 8-position are novel as such. Preferred cyclosporins providing the hapten moiety of such conjugates are in particular those having an activated coupling group as defined under 1.8 to 1.11, 1.14 and 1.15 (formulae IIb and IId) above.

The present invention accordingly also provides:

2.4 An immunogenic conjugate comprising a carrier coupled to a cyclosporin via the α-amino acid residue at position 5-, 6-, 7- or 8- of said cylosporin.

2.5 An immunogenic conjugate comprising a carrier coupled with a cyclosporin having an activated coupling group as defined under any one of 1.8 to 1.11, 1.14 or 1.15 (formulae IIb and IId) above.

2.6 An immunogenic conjugate comprising a carrier coupled with a cyclosporin having a free amino or carboxy group as defined under any one of 1.12 to 1.14 and 1.15 (formulae Ib and Id) above, in particular a cyclosporin as defined under 1.14 above or of formula Id as defined above.

3.11 A monoclonal antibody according to 3.9 above, characterised in that the cyclosporin employed at step a) is a cyclosporin as defined under 2.5 above.

6.1 Antibody reactive with a cyclosporin (including polyclonal antiserum containing antibodies reactive with a cyclosporin) generated in response to an immunogenic conjugate as defined under any one of 2.4 to 2.6 above.

6.2 Antibody according to 6.1 reactive with Cyclosporine, dihydro-[Val]$^2$-Cyclosporine or [Nva]$^2$-Cyclosporine, especially Cyclosporine.

Immunogenic conjugates as defined under 2.5 may be prepared in accordance with the methods of process step vi) above. Immunogenic conjugates as defined e.g. under 2.6 may be prepared by methods as hereinbefore described or by a process comprising:

x) Coupling a carrier to a cyclosporin having an α-amino acid residue bearing a reactive group (i.e. α-amino acid residue having a side chain at the α-carbon atom comprising or bearing a reactive group), e.g. a cyclosporin bearing a free amino or carboxy group as defined under any one of 1.12 to 1.14 and 1.15 (formulae Ib and Id) above.

The above process step may be effected in accordance with techniques known in the art, by linkage of the carrier to the cyclosporin via the intermediary of a coupling reagent. Thus in the case of cyclosporins having a -(D)Lys- residue at the 8-position, conjugates may be obtained by linkage of the carrier, e.g. polypeptide, for example immunoglobulin, to the -(D)Lys-N-ε-atom, employing the carbodiimide procedure [Kellie et al., "Steroid Immunology", ed. Cameron et al., Alpha. Omega, Cardiff, 1975] or by Mannich reaction employing formaldehyde as the coupling reagent.

Suitable carriers include those of the type already referred to in relation to the preparation of conjugates for the production of monoclonal antibodies, in particular high molecular weight polypeptides, especially proteins such a serum albumins, immungobulins and synthetic polymers such as polyglutamic acid.

Regular polyclonal antisera as defined under 6.1, while lacking the fine specificity of monoclonal antibodies as hereinbefore described and defined, are also useful, e.g. as diagnostic/assay kit components, in particular having regard to their improved specificity with respect to cyclosporins as compared with such antisera known from the art. They may be prepared employing essentially conventional techniques, e.g. by a process comprising:

xi) Elliciting an immune response in an appropriate animal species by administration of an immunogenic conjugate as defined under any one of 2.4 to 2.6 above and recovering antisera thus generated.

The above defined process step xi) may be performed e.g. by administration of the immunogenic conjugate to e.g. a mouse, sheep or chicken, e.g. by injection. After an appropriate incubation period the antiserum is recovered and is suitably lyophylised, e.g. for later use in kits, for example as hereinafter described. The period of incubation is suitably chosen to give an antiserum titre of greater than 1:2,000, e.g. in the range of from about 1:7,000 to about 1:10,000, in e.g. regular RIA.

As previously indicated the monoclonal antibodies and polyclonal antisera, as well as labelled cyclosporins of the invention are all of particular utility as components of diagnostic/assay kit systems, e.g. immuno assay kits.

Accordingly, in a yet further aspect the present invention provides:

7. An immuno assay kit or system, e.g. RIA or FIA kit or system, for cyclosporine assay, for example for the assay of a cyclosporin, e.g. Cyclosporine, in subjects receiving cyclosporin, e.g. Cyclosporine, therapy, said kit or system comprising:

A) Antibody or antiserum as defined under any one of 3.1 to 3.11 or 6.1 to 6.2 above, in particular a monoclonal antibody as defined under any one of 3.1 to 3.11 above, and/or B) a labelled derivative of a cyclosporin as defined under any one of 5.1 to 5.3 above, as component of said kit or system.

Kits as defined under 7 are useful for diagnostic purposes, e.g. for determining quantities of a cyclosporin present in blood, blood plasma or urine, e.g. as a means of establishing an appropriate dosaging regimen for patients receiving cyclosporin therapy. Such kits provide an assay means for cyclosporins, e.g. Cyclosporine, of hitherto unmatched sensitivity.

Kits, e.g. RIA and FIA, kits in accordance with the invention may be of entirely conventional type for use in accordance with conventional RIA and FIA assay techniques. Thus RIA kits will suitably comprise in addition to antiserum or antibody, e.g. A) above, an appropriate labelled cyclosporin derivative, e.g. B) above, and C) cyclosporin standard The labelled cyclosporin derivative will be complementary to the cyclosporin to be assayed. Suitably it will be a labelled derivative as defined under B) above, e.g. where Cyclosporine is to be assayed it will suitably be a labelled derivative of [(D)Lys]$^8$-Cyclosporine. However it may also be any other labelled complementary cyclosporin, for example where Cyclosporine is to be assayed, tritiated Cyclosporine. The cyclosporin standard C) will generally be a solution or the like comprising a known quantity of the cyclosporin to be assayed.

In use, e.g. lyophilised, antiserum/antibody is dissolved and incubated together with e.g. component B) and with either the sample to be assayed or component C). Incubation is preferably effected with cooling e.g. at 4° C. The pH of the incubating mixture is preferably kept in the range of from about 5 to 8, e.g. at about pH 7 or 8, preferably with the aid of a buffering agent such as a citrate or tris buffer.

Incubation conveniently lasts for at least 2 hours, e.g. from about 6 to about 12 hours. After incubation the fraction of e.g. component B) bound to the antibody is separated from the unbound fraction, e.g. by the use of charcoal such as dextran-coated charcoal. The unbound fraction adsorbs onto the charcoal and may then be separated by filtration or by centrifugation. The amount of radioactivity in one fraction is then measured by standard techniques, e.g. by liquid scintillation counting after the addition of a secondary solute. The proportion of component B) bound to the antibody is inverseley proportional to the amount of cyclosporin in the unknown plasma sample. For quantitive analysis, it is usual to prepare a standard calibration curve by analysing solutions of the cyclosporin of known concentration.

FIA kits in accordance with the invention may be e.g. of the kind wherein antibodies are bound to a light scavenger and which depend upon competition between a fluorescent cyclosporin (e.g. a fluorescently labelled derivative in accordance with the invention) and the antibody.

Alternatively assay kits/systems as defined under 7 above may be based on any of the conventional ELISA systems known in the art.

The following examples are illustrative of the present invention:

EXAMPLE 1

Preparation of [(D)Lys⁸]-Cyclosporine a) A solution of 6.4 g H-MeLeu-MeLeu-MeVal-OBzl maleinate in $CH_2Cl_2$ (200 ml) and $H_2O$ (100 ml) is adjusted to pH 8 using solid $K_2CO_3$. After extracting 2×, each time with $CH_2Cl_2$ (200 ml), the organic phase is dried over $Na_2SO_4$ filtered and evaporated to dryness to yield free H-MeLeu-MeLeu-MeVal-OBzl as a crystalline residue.

b) (N-ε-BOC)-FMOC-(D)Lys (6.25 g) is dissolved in $CHCl_3$ (100 ml) and N-methylmorpholine (2.95 g) is added with stirring. After cooling the solution to $-20°$, pivaloyl chloride (1.75 g) is added dropwise, and the reaction mixture is stirred for 6 hours at $-20°$. A solution of H-MeLeu-MeLeu-MeVal-OBzl (6.34 g) in $CHCl_3$ (20 ml) is added to the anhydride solution dropwise and stirred for 17 hours at $-20°$ to complete reaction. After diluting the $CHCl_3$ solution with further $CHCl_3$ (200 ml), the mixture is shaken with saturated $NaHCO_3$ solution (100 ml). The organic phase is dried over $Na_2SO_4$, filtered and the solvent evaporated to dryness.

The obtained oily residue is purified chromatographically, using 25× the amount of silica gel (particle size 0.063–0.20 mm) and methylene chloride with additional 3% methanol as eluant:$[α]_D^{20} = -114.2°$ (c=1.0 in $CHCl_3$).

c) (N-ε-BOC)-FMOC-(D)Lys-MeLeu-MeLeu-MeVal-OBzl (8.8 g) dissolved in absolute ethanol (400 ml) is hydrogenated with 10% palladium/C catalyst (0.6 g) in a Gastar hydrogenator until the theoretical quantity of $H_2$ is taken up (214 ml). After evaporating off the solvent, the residue is purified chromatographically using 50× the quantity of silica gel (0.063–0.20 mm) and methylene chloride plus 7% methanol as eluant: $[α]_D^{20} = 129.1°$ (c=1.0 in $CHCl_3$).

d) (N-ε-BOC)-FMOC-(D)Lys-MeLeu-MeLeu-MeVal-OH (7.1 g) and H-MeBmt-αAbu-Sar-MeLeu-Val-MeLeu-Ala-OBzl (7.4 g) are dissolved in methylene chloride (100 ml), and N-methylmorpholine (1.72 g) and Castro reagent (Bt-Op(NMe₂)₃⁺PF₆³¹) (5.6 g) are added at room temperature (25°). reaction mixture is stirred for 3 days at room temperature, then the solution is diluted with methylene chloride (200 ml) and shaken with saturated $NaHCO_3$ solution (100 ml). The organic phase is dried over $Na_2SO_4$, filtered and evaporated to dryness. The obtained oily residue is purified chromatographically on silica gel (500 g) (0.06–0.20) using methylene chloride plus 3% methanol as eluant: $[α]_D^{20} = -143.8°$ (c=1.0 in $CHCl_3$).

e) (N-ε-BOC)-FMOC-(D)Lys-MeLeu-MeLeu-MeVal-MeBmt-αAbu-Sar-MeLeu-Val-MeLeu-Ala-OBzl (5.54 g) are stirred for a total of 4 hours at room temperature in a solution of methylene chloride (50 ml) and piperidine (10 ml). The solvent is evaporated and the obtained oil chromatographed on Sephadex LH20 (300 g) using methylene chloride plus 3% methanol as eluant: $[α]_D^{20} = -165.2°$ (c=1.0 in $CHCl_3$).

f) 0.2N NaOH (24 ml) is added to (N-ε-BOC)-H-(D)Lys-MeLeu-MeLeu-MeVal-MeBmt-αAbu-Sar-MeLeu-Val-MeLeu-Ala-OBzl (6.48 g) dissolved in ethanol (75 ml). After 7 hours the solution is adjusted to pH 4 by dropwise addition of 2N HCl with cooling. After evaporation of the solvent, the obtained residue is shaken in $CH_2Cl_2$ (200 ml) and saturated $NaHCO_3$ (200 ml) solution. After extraction of the aqueous phase 2×, each time using methylene chloride (200 ml), the organic phase is dried over $Na_2SO_4$, filtered off and evaporated. The product is purified chromatographically on silica gel (300 g) (0.06–0.20 mm) using methylene chloride plus 20% methanol as eluant: $[α]_D^{20} = -169.9°$ (c=1.0 in $CHCl_3$).

g) [Process step v)]

Dimethylaminopyridine (147 mg) is added with stirring to (N-ε-BOC)-H-(D)Lys-MeLeu-MeLeu-MeVal-MeBmt-αAbu-Sar-MeLeu-Val-MeLeu-Ala-OH (413 mg) dissolved in methylene chloride (2000 ml). Propane phosphonic acid anhydride [(0.19 g) 50% solution in $CH_2Cl_2$] is added and the reaction mixture is stirred for 24 hours at 25°. The obtained solution is washed with saturated $NaHCO_3$ solution (200 ml), the organic phase is dried over $NaSO_4$, filtered off and evaporated, and purified chromatographically on silica gel (300 g) (0.062–0.20) using methylene chloride plus 5% methanol as eluant: $[α]_D^{20} = -198.3$ (c=1.0 in $CHCl_3$).

h) [Process step iv)]

[(N-ε-BOC)-(D)Lys]⁸-Cyclosporine (842 mg) is cooled to $-20°$ with trifluoroacetic acid (25 ml) and stirred together for 4 hours at $-20°$. The reaction solution is mixed with ice, sat. $K_2CO_3$ (10 ml) and extracted 3× with methylene chloride (200 ml). The organic phase is dried over $Na_2SO_4$, filtered and the solvent is evaporated. The obtained crude product is chromatographed on Sephadex LH20 (200 g) using methylene chloride plus 1% methanol as eluant to yield the title compound [(D)Lys]⁸-Cyclosporine: $[α]_D^{20} = -204.3°$ (c=1.0 in $CHCl_3$).

The product compound may also be converted into salt form in accordance with standard techniques. Typical salts include [(D)Lys]⁸-Cyclosporine hydrochloride: $[α]_D^{20} = -203°$ (c=1.0 in $CHCl_3$), and [(D(Lys)⁸-Cyclosporine trifluoroacetate: $[α]_D^{20} = -203°$ (c=1.0 in $CHCl_3$).

EXAMPLE 2

Preparation of [(N-ε-hydroxysuccinyl)-(D)Lys]⁸-Cyclosporine: [Process step iii)]

255 mg of [(D)Lys]⁸-Cyclosporine produced in accordance with example 1 are dissolved in 20 ml pyridine and 36 mg succinic anhydride are added. The obtained solution is stirred for ca. 14 hrs. at room temperature and the pyridine fully evaporated under vacuum at max. 40° C. The obtained oily residue is chromatographed on 55 g Sephadex LH 20 employing methylene chloride+2% methanol and collected in 10 ml fractions. The pure title compound is obtained from fractions 15 through 23.

NMR spectroscopy shows succinyl protons at 2.50 and 2.70 ppm (broad signals) and a signal for —CH₂—NH—COCH₂CH₂COOH at 3.25 ppm.

EXAMPLE 3

Preparation of
[(O-hydroxysuccinyl)-Thr]²-Cyclosporine: [Process step iii)]

6.05 g [Thr]²-Cyclosporine is dissolved in 20 ml pyridine and 3.66 g 4-dimethylamino-pyridine and 1.5 g succinic anhydride are added at 75° C. The reaction mixture is stirred for 4 hours at 75° C. and then diluted with 500 ml CH₂Cl₂, washed 5×, each time with 50 ml 2N HCl, and 1× with 150 ml H₂O. The organic phase is extracted, dried over Na₂SO₄ and evaporated and purified chromatographically using 250 g silica gel (0.040-0.062 mm) with acetic acid as eluant.

EXAMPLE 4

Preparation of
[(N-ε-succinimidooxysuccinyl)-(D)Lys]⁸-Cyclosporine: [Process step i)]

50 mg of [(N-ε-hydroxysuccinyl)-(D)Lys]⁸-Cyclosporine produced in accordance with example 2, 14 mg N-ethyl-N'-(dimethylaminopropyl)-carbodiimide HCl, 23.8 mg N-hydroxysuccinimide and 24.6 mg triethylamine are stirred for 2 hrs. at room temperature in 2 ml methylene chloride to yield a clear colourless solution. The obtained solution is diluted with 50 ml methylene chloride and 10 ml H₂O and 1N HCl is added dropwise until pH 6. A two phase mixture develops and this is shaken thoroughly between each addition of HCl. The organic phase is finally shaken with 10 ml dilute NaHCO₃ solution and dried over Na₂SO₄, filtered and the solvent evaporated off to yield the title compound.

The NMR spectrum exhibits succinyl protons at 2.50 and 2.75 ppm (J=5 cps) and N-succinimido protons at 2.18 and 2.19 ppm (2S). The residue at the 8-position has the following structure:

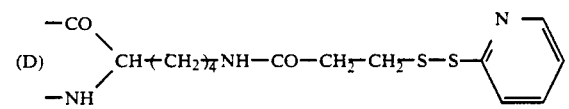

EXAMPLE 5

Preparation of
[(O-succinimidooxysuccinyl)-Thr]²-Cyclosporine: [Process step i)]

54 mg triethylamine, 98 mg N-hydroxysuccinimide and 102 mg N-ethyl-N'-(3-dimethylaminopropyl)-carbodiimide are added to a solution of 200 mg of [(O-hydroxysuccinyl)-Thr]²-Cyclosporine produced in accordance with example 3 in 10 ml methylene chloride, addition being effected at 20° C. with rigorous exclusion of moisture. The reaction mixture is stirred for 6 hours at room temperature, diluted with 200 ml methylene chloride and shaken with 50 ml H₂O. The aqueous phase in adjusted to pH 5-6 by drop-wise addition of 1N HCl and shaken. The aqueous phase is extracted with 100 ml methylene chloride and the organic phases washed with 0.1N NaHCO₃, dried over Na₂SO₄, filtered and evaporated. The residue is purified chromatographically using 110 g silica gel with ethylacetate as eluant to yield the title compound: $[\alpha]_D^{20} = -178°$ (c=1.0 in CHCl₃). ¹H-NMR in CDCl₃ shows succi protons at 2.80 as a singlet and succinyl protons at 2.60 ppm as a multiplet. The residue at the 2-position has the following structure:

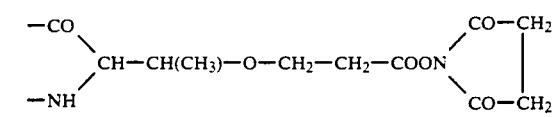

EXAMPLE 6

Preparation of
[(N-(3-(2-pyridyl)dithio)propion-1-yl)-(D)Lys]⁸-Cyclosporine: [Process step ii)]

35 mg succinyl-3-[(2-pyridyl)dithio]propionate are added to a solution of 126 mg [(D)Lys]⁸-Cyclosporine in 10 ml methylene chloride at 20° C. and with rigorous exclusion of moisture. The reaction mixture is stirred for 6 hours at room temperature, diluted with 200 ml methylene chloride and shaken with 50 ml saturated NaHCO₃. The aqueous phase is extracted with 150 ml methylene chloride, the organic phases washed with H₂O, dried over Na₂SO₄, filtered and evaporated. The amorphous residue is purified chromatographically using 100 g silica gel with methylene chloride/methanol (95:5) as eluant to yield the pure title compound: $[\alpha]_D^{20} = -165°$ (c=1.0 in CHCl₃).

The residue at the 8-position has the formula

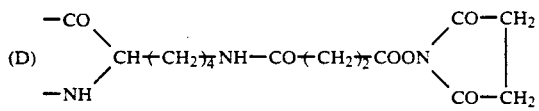

EXAMPLE 7

Preparation of immunogenic cyclosporin-carrier conjugates of the type defined under 2.1 above: [Process step vi)]

7.1 Conjugate with Chicken Y-Globulin 10 mg of [(N-ε-succinimidooxysuccinyl)-(D)Lys]⁸-Cyclosporine produced in accordance with the method of example 4 in 0.2 ml dimethylformamide are added to 100 mg chicken γ-globulin in 4 ml NaHCO₃ (1.5% w/v, pH 8.1). The reaction mixture is stirred for ca. 2 hours at room temperature and the obtained conjugate purified by dialysis against phosphate buffered saline.

7.2 Conjugate with Chicken Ovalbumin 10.7 mg [(O-succinimidooxysuccinyl)-Thr]²-Cyclosporine produced in accordance with example 5 and additionally containing 10% dititrated material (1 - 2 μCi/mg - obtained analogously to example 5, but using tritrated [Thr]²-Cyclosporine as starting material) in 100 μl dimethylformamide are added with vigorous stirring to 30.45 mg chicken ovalbumin in 2 ml, 1.5% NaHCO₃ buffer (molar excess cylosporin/ovalbumin=10.68). The reaction mixture is stirred for 2 hours at ambient temperature and the obtained conjugate purified by dialysis 3× against phosphate buffered saline for 18 hours at 4° C. For the conjugate product 55.7% of input radioactivity is found bound to ovalbumin, indicating a binding ratio of 5.95 cyclosporin/ovalbumin.

Covalent binding of cyclosporin to ovalbumin was evaluated by acetone precipitation of 3 conjugate aliquots . 39.5% of radioactivity corresponding to non-covalently bound cyclosporin is determined in the acetonic supernatant, giving a final covalent coupling ratio of 3.6 cyclosporin/ovalbumin. The obtained conjugate was aliquoted and kept at −20° C.

Similar conjugates may be prepared analogously to examples 7.1 and 7.2 above, but employing the product of example 6 as the cyclosporin starting material.

EXAMPLE 8

Preparation of immunogenic cyclosporin-carrier conjugates of the type defined under 2.4/2.6 above: [Process step (x)]

8.1 Conjugate with Guinea pig IgG

Guinea pig IgG (30 mg) are dissolved in 0.1M bicarbonate buffer (pH 9, 0.5 ml) and added to a solution of $[(D)Lys]^8$-Cyclosporine (1 mg) prepared in accordance with the method of example 1, in the same buffer (0.5 ml) and a few drops of 1% acetic acid are added. Coupling is effected by subsequent addition of 2 portions of N-ethyl-N'-(3-dimethylaminopropyl)carbodiimide hydrochloride (each portion=100 mg). The reaction product is prepared for injection 24 hours later by multiple dialysis against water followed by lyophilisation.

8.2 Conjugate with Rabbit IgG $[(D)Lysl]^8$-Cyclosporine (10 mg), prepared in accordance with the method of example 1, is dissolved in 0.1 ml of an ethanolic solution of 6.9 μg (=0.1 mCi) tritiated $[(D)Lys]^8$-Cyclosporine. 0.1 ml pyridine and 0.1 ml 35% formaldehyde are added and the whole is held for 30 mins. at room temperature. 20 mg rabbit IgG in 0.02M phosphate-buffered saline (1 ml) and 0.3 ml pyridine are then added and the reaction allowed to stand for ca. 14 hrs. at room temperature. The obtained conjugate is dialysed against 30% pyridine, 10% pyridine and, finally, 0.005M phosphate-buffered saline. The coupling rate of the conjugate is 1:11.4.

EXAMPLE 9

Production of hybridoma cell-lines, producing monoclonal antibodies reactive with Cyclosporine: [Process step viii)]

9.1 Employing the conjugate of example 7.1 a) Immunisation

Female Balb/c mice (20–25 g) each receive 100 μG of the immunogenic conjugate product of example 7.1 in 0.2 ml complete Freund adjuvant, administered by i.p. injection. After 2 weeks a second booster injection comprising 50 μg of the product of example 7.1 emulsified in 0.2 ml complete Freund adjuvant is administered, again by i.p. injection. The presence of antibodies reactive to Cyclosporine in the serum of treated mice is confirmed by regular RIA assay employing tritium labelled Cyclosporine as tracer.

b) Hybridoma Generation

Mice obtained in step a) exhibiting maximum Cyclosporine reactive antibody titres receive a booster injection comprising 20 μg of the product of example 3.2 in saline (0.85% w/v) administered i.v. The mice are sacrificed on the 4th. day, and spleen cells, isolated and fused with mouse (Balb/C) myeloma cells in accordance with the methods described by S. Fazekas et al., J. Immunol. Methods, 35, 1–21 (1980).

Growing hybridomas are screened for production of antibody reactive to Cyclosporine by regular RIA assay technique employing tritium labelled Cyclosporine as tracer, and exhibiting low cross-reactivity with Cyclosporine 17, again using regular RIA assay technique with tritum labelled Cyclosporine as tracer and Cyclosporine 17 as competitive ligand.

One selected hybridoma line, J19.2, is found to produce a monoclonal antibody reactive with Cyclosporine and having low cross-reactivity with Cyclosporine 17. The antibody is characterised as belonging to the class IgG, subclass $IgG_1$. The obtained $IC_{50}$ value for reactivity with Cyclosporine in RIA is 6.7 ng/ml, compared with 280 ng/ml for Cyclosporine 17. Cross-reactivity with Cyclosporine 17 is thus of the order of 2% only. Determined affinity constant with respect to Cyclosporine is of the order of $10^{-9}$ mol/liter.

The said hybridoma line has been deposited with the National Collection of Animal Cell Cultures, (now known as the European Collection of Animal Cell Cultures) PHLS Centre for Applied Microbiology and Research, Porton Down, Salisbury, SP4 OJG. U.K. under the accession no. 85 06 14 01 (date deposit 13. Jun. 1985).

It will be appreciated that by application of the techniques of the present invention as generally taught herein, in particular the employment of cyclosporins having an activated coupling group, e.g. as hereinbefore defined under any one of 1.1 to 1.11, 1.14 or 1.15 (formulae IIa, IIb, IIc or IId) for the preparation of immunogenic conjugates, and proceeding e.g. analogously to the general methods of this example, hybridoma lines/monoclonal antibodies may. readily be prepared which, though not identical with the specific product hybridoma line/monoclonal antibody of this example, will meet the same essential criteria, e.g. exhibit equivalent or even improved characteristics to those described above. This will be apparent from results evidenced in the following example.

9.2 Employing the conjugate of example 7.2 a) Immunisation

Mice (Balb/c) each receive 100 μg of the immunogenic conjugate product of example 7.2 in 200 μl phosphate buffered saline/Freund adjuvent (1:1). The first administration (complete Freund adjuvent) is effected s.c. in the hind foot pad, near the tail and near the neck. After three weeks, second and third administrations follow (incomplete Freund adjuvent) effected s.c. on the back and i.m. in the hind legs respectively. Blood samples are collected 1 week after both the 2nd and 3rd administrations.

Mice are selected for further use on the basis of the following measured antisera criteria:
1. Titre in liquid phase RIA and in ELISA;
2. Apparent isotype distribution ($IgG_1$ only or $IgG_{1+2a+2b}$ in ELISA);
3. Relative avidity in ELISA;
4. Capacity to discriminate between Cyclosporine and Cyclosporine 17 and Cyclosporine 18 in competitive ELISA.

Selected mice are given booster injections on days −3, −2 and −1 prior to fusion using 100 μg of the immunogenic conjugate product of example 7.2 in 200 μl, 9% NaCl, by i.p. (50%) and i.v. (50%) injection on day −3, and i.p. (100%) on days −2 and −1.

b) Hybridoma generation $2.5 \times 10^{-7}$ or $5 \times 10^{-7}$ spleen cells from each mouse are fused with $5 \times 10^{-7}$ mouse (Balb/c) myeloma cells using PEG 4000 and distributed into 24×24 wells.

Culture supernatants are screened in ELISA for the presence of antibodies recognising [Thr]²-Cyclosporine coupled to bovine serum albumin (prepared analogously to example 7.2) and/or [(D)Lys]⁸-Cyclosporine coupled to bovine serum albumine (prepared analogously to example 7.1) in preference to free bovine serum albumin as negative control. Selected IgG producing hybridoma lines are cloned to guarantee monoclonality.

Ability of monoclonal antibodies produced by hybridoma lines obtained, to distinguish/discriminate between (a) Cyclosporine and (b) Cyclosporine 17 and Cyclosporine 18 is tested in a competition format of indirect ELISA as described by Quesniaux et al., Immunology Letters, 9, 99–104, (1985), in a variety of buffer systems including: phosphate buffered saline at pH 7.5, with and without 0.03% Tween 20; and Tris at pH 7.5, with 0.03% Tween and without NaCl. Optimal conditions for discrimination are generally observed in phosphate buffered saline at pH 7.5, with 140 mM NaCl and 0.03% Tween 20. Of 9 clone lines examined 7 produce monoclonal antibodies discriminating between (a) Cyclosporine and (b) Cyclosporines 17 and 18. For 6 the IC$_{50}$ ratio of Cyclosporine 17 compared to Cyclosporine is ca. 35× or greater.

EXAMPLE 10

Production of regular polyclonal antisera reactive with Cyclosporine [Process step xi)]

Sheep are immunised by hind limb, intramuscular injections 10× at intervals of approx. 14 days. The injections comprise a lyophylisate of the immunogenic protein conjugate product of example 8.1 (3 mg), Alu-gel S (0.2 ml) and Freund adjuvant (0.6 ml). The final titre obtained against tritiated Cyclosporine is 1/100,000 as measured by RIA.

Polyclonal antisera recovered are found to exhibit improved discrimination between Cyclosporine and its metabolite Cyclosporine 17 as compared with polyclonal antisera obtained using [Thr]²-Cyclosporine-IgG conjugates known in the art, e.g. as employed in current Cyclosporine RIA assay kits. Thus for antisera obtained in accordance with the present example, cross-reactivity with Cyclosporine 17 is of the order of ca. 18% as compared with ca. 42.0% for known polyclonal antisera.

EXAMPLE 11

Preparation of labelled derivatives of cyclosporins as defined under 5.1 above: [Process step ix)]

11.1:

Preparation of [N- -TRITC-(D)Lys]⁸-Cyclosporine

[(D)Lys]⁸-Cyclosporine (15 mg) produced in accordance with example 1 are dissolved in methylene chloride (2 ml). Rhodamine isothiocyanate (TRITC) (5.3 mg) is added and the reaction mixture allowed to stand at −7° C. for 17 hours. The intensively-red-coloured solution is directly chromatographed on Sephadex LH20 (20 g) with methylene chloride and 0.5% methanol. Fractions are collected in 10 ml portions.

The title compound is recovered as an oil from fractions 5 to 7 and 10 to 14: UV absorption: 300 nm/fluorescence emission: 540 nm. The residue at the 8-position has the structure:

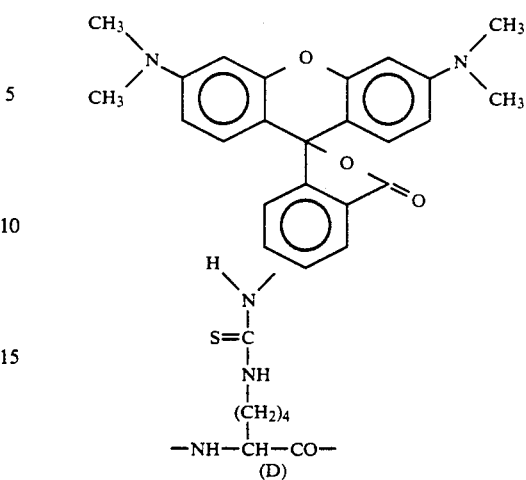

11.2:

Preparation of [N-ε-Dansyl-(D)Lys]⁸-Cyclosporine

[(D)Lys]⁸-Cyclosporine (232 mg) produced in accordance with example 1 is dissolved in chloroform (15 ml). Ethyl diisopropylamine (7.3 mg) and dansyl chloride (99.5 mg) are added and the reaction mixture is stirred for 2 hours. The product is chromatoraphed directly on Sephadex LH20 (100 g) with methylene chloride and 0.5% methanol. Fractions are collected in 10 ml portions.

The collected fractions are evaporated and the resulting product re-chromatographed using silica gel (0.06–0.20 mm) (100 g) with methylene chloride and 5% methanol. Fractions are collected in 15 ml portions.

Fractions 28-44 yield pure product: $[\alpha]_D^{20} = -183.8°$, c = 1.08 in CHCl$_3$.

11.3:

Preparation of ¹²⁵Iodinated Derivative of [(D)Lys]⁸-Cyclosporine

Title compound is prepared analogously to the methods described by Bolton and Hunter [Biochem. J. 133, 529 (1973)] by attachment of a p-OH-phenylpropionyl residue to the N-ε-atom of the residue at the 8-position of [(D)Lys]⁸-Cyclosporine prepared in accordance with example 1. The ¹²⁵I label is carried in the phenyl ring of the p-OH-phenylpropionyl residue

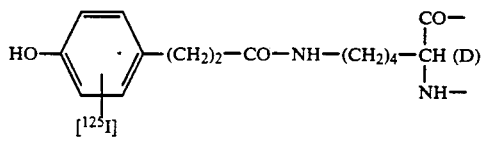

Purification is effected by HPLC on a 4×250 column of RP18 with a linear gradient and using 10–30% n-propanol/0.2% trifluoroacetic acid in 5% acetic acid/0.2% trifluoroacetic acid as liquid phase.

We claim:

1. A monoclonal antibody which binds to cyclosporine and exhibits less than about 5% cross-reactivity as measured in an ELISA assay, to at lest one of the cyclosporine metabolites selected from the group consisting of: cyclosporine 1, 8, 9, 10, 16, 17, 18, and 21.

2. A hybridoma cell line which produces a monoclonal antibody according to claim 1.

3. A monoclonal antibody which binds to cyclosporine and exhibits less than about 5% cross-reactivity, as measured in an ELISA assay, to a cyclosporine metabolite wherein said cyclosporine metabolite is Cyclosporin 17 or Cyclosporin 18.

4. A hybridoma cell line which produces a monoclonal antibody according to claim 3.

5. A monoclonal antibody, which binds to cyclosporine and exhibits less than about 5% cross-reactivity, as measured in an ELISA assay, to one or more of the cyclosporine metabolites selected from the group consisting of cyclosporine 1, 8, 9, 10, 16, 17, 18 and 21 produced by the process of:
 a) reacting a carrier molecule with a cyclosporin having an α-amino acid residue bearing an activated coupling group, said activated coupling group being a group capable of direct reaction with the carrier molecule, to provide a covalently linked immunogenic conjugate;
 b) administration of said immunogenic conjugate to an appropriate animal species to effect immunogenic challenge and recovery of antibody-producing cells sensitized to said conjugate;
 c) immortalization of said antibody-producing cells; and
 d) recovery of monoclonal antibody from a selected immortalized cell line thus established.

6. An immunoassay kit or system for cyclosporin assay comprising:
 a) an antibody according to claim 1; or
 b) a labelled derivative of a cyclosporin wherein the residue at position 8 is -(D)Lys-.

* * * * *